(12) United States Patent
Furumoto et al.

(10) Patent No.: US 9,486,465 B2
(45) Date of Patent: Nov. 8, 2016

(54) ATTRACTANT FOR BONE MARROW STEM CELLS AND METHOD FOR ATTRACTING BONE MARROW STEM CELLS

(71) Applicants: PIAS CORPORATION, Osaka-shi, Osaka (JP); OSAKA UNIVERSITY, Suita-shi, Osaka (JP)

(72) Inventors: Tadashi Furumoto, Suita (JP); Koichi Nakaoji, Kobe (JP); Kazuhiko Hamada, Kobe (JP); Noriyasu Ozawa, Kobe (JP); Yuta Inami, Kobe (JP); Misaki Toyoshima, Kobe (JP); Kosuke Fujita, Kobe (JP); Akito Maeda, Suita (JP); Yasufumi Kaneda, Suita (JP); Katsuto Tamai, Suita (JP)

(73) Assignees: Pias Corporation, Osaka (JP); Osaka University, Osaka (JP)

( * ) Notice: Subject to any disclaimer, the term of this patent is extended or adjusted under 35 U.S.C. 154(b) by 0 days.

(21) Appl. No.: 14/396,142

(22) PCT Filed: May 31, 2013

(86) PCT No.: PCT/JP2013/065223
§ 371 (c)(1),
(2) Date: Oct. 22, 2014

(87) PCT Pub. No.: WO2013/190978
PCT Pub. Date: Dec. 27, 2013

(65) Prior Publication Data
US 2015/0111842 A1  Apr. 23, 2015

(30) Foreign Application Priority Data
Jun. 21, 2012 (JP) ................. 2012-139442

(51) Int. Cl.
A61K 31/7032 (2006.01)
A61K 31/353 (2006.01)
A61K 31/7024 (2006.01)
A61K 36/00 (2006.01)

(52) U.S. Cl.
CPC ......... *A61K 31/7032* (2013.01); *A61K 31/353* (2013.01); *A61K 31/7024* (2013.01); *A61K 36/00* (2013.01)

(58) Field of Classification Search
CPC ........... A61K 31/353; A61K 31/7024; A61K 31/7032; A61K 31/23; A61K 36/00
USPC .................. 514/25, 453; 536/18.2; 549/382; 435/375
See application file for complete search history.

(56) References Cited

U.S. PATENT DOCUMENTS

| 4,466,961 A | 8/1984 | Szijjarto et al. |
| 5,525,635 A * | 6/1996 | Moberg ............ A61K 8/345 514/557 |
| 2009/0110709 A1* | 4/2009 | Mitts ............ A61K 8/02 424/422 |

FOREIGN PATENT DOCUMENTS

| CN | 101525357 A | 9/2009 |
| CN | 10176219 A | 6/2010 |
| WO | 2010/129524 A2 | 11/2010 |

OTHER PUBLICATIONS

Killday et al, Journal of Natural Products, 2011, 74, 1833-1841.*
Satoh et al, Biochemical Pharmacology, 1997, 53, 611-614.*
Ezaki et al, Planta Medica, 1985, 1, 34-38.*
Gurtner et al, Ann. Rev. Med., 2007, 58, 299-312.*
Lopez et al, Life Science, 2008, 82, 977-982.*
Satoh K, et al., "Inhibition of Na+, K(+). . . " Biochem Pharmacol., Feb. 21, 1997, vol. 53 No. 4, pp. 611-614.
Ezaki N. et al., "Pharmacological studies on Linderae . . . " Planta Med., Feb. 1985, vol. 1. pp. 34-38.
Shivananda NB et al., "Wound-healing properties of . . . " Phytother Res., Feb. 9, 2011, vol. 25 No. 8, pp. 1201-1208.
Seeram NP et al., "Blackberry, black raspberry, . . . " J Agric Food Chem., Dec. 13, 2006, vol. 54 No. 25, pp. 9329-9339.
Killday KB et al., "Bioactive A-type proanthocyanidins . . . " J Nat Prod., Aug. 29, 2011, vol. 74 No. 9, pp. 1833-1841.
International Preliminary Report and Written Opinion issued Dec. 31, 2014 in connection with parent PCT Application No. PCT/JP2013/065223.
A. Bouaziz, et al., "Cinnamtannin B-1 from bay wood exhibits antiapoptotic effects in human platelets", Apoptosis, 2007, vol. 12, pp. 489-498.
Elisabetta Stringano, et al., "Simple solution for a complex problem: Proanthocyanidins, galloyl glucoses and ellagitannins fit on a single calibration curve in high performance-gel permeation chromatography", Journal of Chromatography A, 2011, vol. 1218, pp. 7804-7812.
Chinese Office Action issued Nov. 4, 2015 in connection with related Chinese Application No. 201380031816.4.

* cited by examiner

*Primary Examiner* — Ganapathy Krishnan
(74) *Attorney, Agent, or Firm* — Berliner & Associates

(57) ABSTRACT

Provided are an attractant for bone marrow stem cells containing at least one of cinnamtannin B1 and pentagalloylglucose, and a method for attracting bone marrow stem cells in which bone marrow stem cells are attracted by the attractant.

5 Claims, 2 Drawing Sheets

ATTRACTANT FOR BONE MARROW STEM CELLS AND METHOD FOR ATTRACTING BONE MARROW STEM CELLS

CROSS-REFERENCE TO RELATED APPLICATION

This application claims priority to Japanese Patent Application No. 2012-139442, the disclosure of which is invoked herein in its entirety. The contents of the application in Japan are incorporated herein by reference

FIELD

The present invention relates to an attractant for bone marrow stem cells and a method for attracting bone marrow stem cells.

BACKGROUND

Bone marrow stem cells are known as cells that are generated in bone marrow and have not yet undifferentiated, and that can differentiate into cells of various body tissues. Further, attention has been given to bone marrow stem cells as being capable of recovering a lost function of a tissue by differentiating into cells of the tissue under the influence of a differentiation inducer that induces differentiation.

Specifically, attention has been given to bone marrow stem cells as being capable of differentiating into tissue cells under the influence of a differentiation inducer, for example, after they migrate from the bone marrow to an inflamed tissue or a damaged tissue through the bloodstream.

Conventionally, various differentiation inducers that are capable of causing differentiation of bone marrow stem cells into various cells are known. For example, a fibroblast growth factor (Fibroblast Growth Factor: FGF) and a platelet-derived growth factor (Platelet-Derived Growth Factor: PDGF) that can cause bone marrow stem cells to differentiate into heart muscle cells are known (Patent Literature 1).

CITATION LIST

Patent Literature

Patent Literature 1: WO 2005/063967 A1

SUMMARY

Technical Problem

However, though having performance to cause differentiation of bone marrow stem cells into cells of a specific tissue, differentiation inducers of this type do not necessarily have sufficient performance to attract bone marrow stem cells, for example, to attract bone marrow stem cells circulating inside the body through the bloodstream to a specific body tissue, which is a problem.

In view of such a problem, it is an object of the present invention to provide an attractant for bone marrow stem cells having excellent performance to attract bone marrow stem cells. Further, it is another object of the present invention to provide a method for attracting bone marrow stem cells with excellent performance to attract bone marrow stem cells.

Solution to Problem

An attractant for bone marrow stem cells according to the present invention contains at least one of cinnamtannin B1 and pentagalloylglucose.

In a method for attracting bone marrow stem cells according to the present invention, bone marrow stem cells are attracted by the attractant.

DESCRIPTION OF EMBODIMENTS

Figure 1:
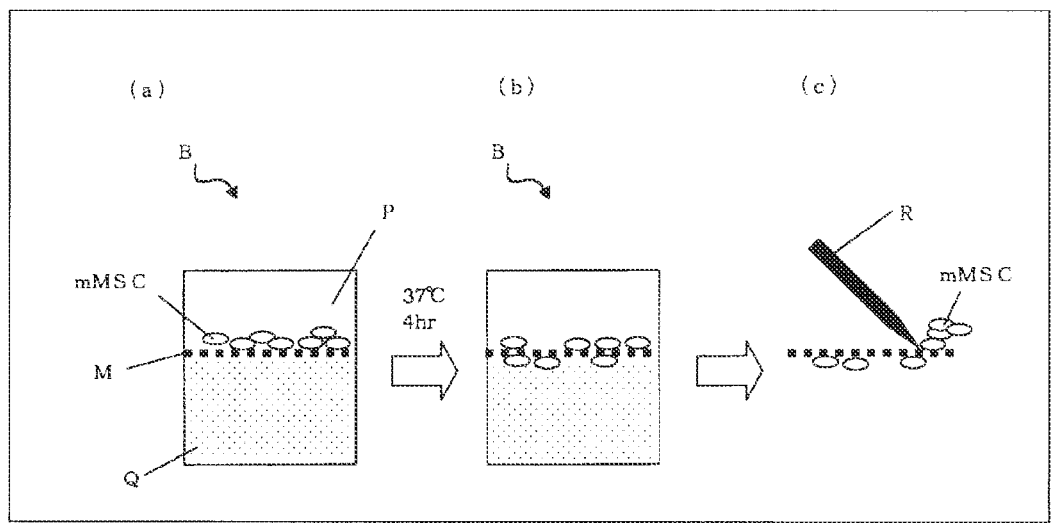
FIG. 1 is a view schematically showing the process of a cell attraction test in vitro.

Hereinafter, an embodiment of an attractant for bone marrow stem cells according to the present invention is described.

The attractant for bone marrow stem cells of this embodiment contains at least one of cinnamtannin B1 and pentagalloylglucose.

Cinnamtannin B1 is a compound having a molecular structure represented by the following formula (1).

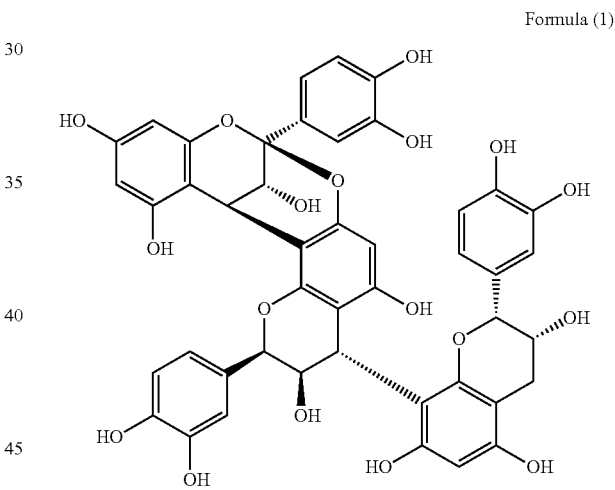

Formula (1)

The concentration of cinnamtannin B1 contained in the attractant for bone marrow stem cells is not specifically limited. The concentration, for example, is 0.001 to 100 wt %.

The attractant for bone marrow stem cells may contain a solvent such as a pH buffer and water, a surfactant, a preservative, oils, polyhydric alcohols, or a water-soluble polymer compound, other than cinnamtannin B1.

The attractant for bone marrow stem cells containing cinnamtannin B1, for example, is produced by dissolving commercially available cinnamtannin B1 into a suitable solvent.

Alternatively, the attractant for bone marrow stem cells containing cinnamtannin B1, for example, is produced by extraction of a cinnamtannin B1-containing portion of a plant such as *laurus nobilis* (*Laurus nobilis* L.), lingonberry (*Vaccinium vitis-idaea*), arameria *laevigata*, cinnamon (*Cinnamomum zeylanicum*), lindera umbellata (*Lindera umbellate*), or *Metaxya rostrata*.

On the other hand, pentagalloylglucose is a compound having a molecular structure represented by the following formula (2).

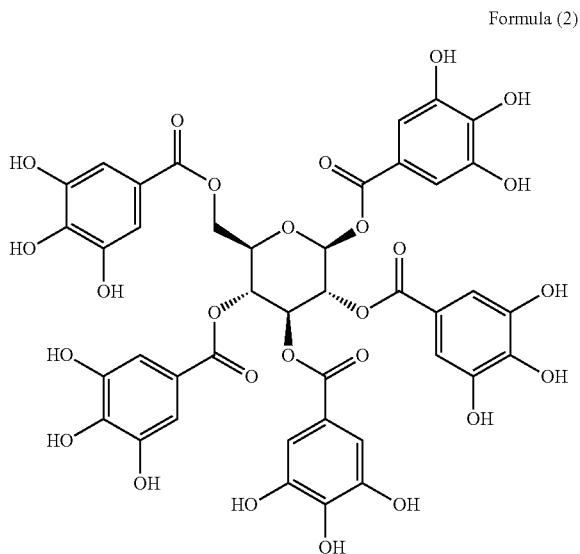 [SMILES: O=C(OC[C@H]1O[C@@H](OC(=O)c2cc(O)c(O)c(O)c2)[C@H](OC(=O)c2cc(O)c(O)c(O)c2)[C@@H](OC(=O)c2cc(O)c(O)c(O)c2)[C@@H]1OC(=O)c1cc(O)c(O)c(O)c1)c1cc(O)c(O)c(O)c1]

Formula (2)

The concentration of pentagalloylglucose contained in the attractant for bone marrow stem cells is not specifically limited. The concentration, for example, is 0.001 to 100 wt %.

The attractant for bone marrow stem cells may contain a solvent such as a pH buffer and water, a surfactant, a preservative, oils, polyhydric alcohols, or a water-soluble polymer compound, other than pentagalloylglucose.

The attractant for bone marrow stem cells containing pentagalloylglucose, for example, is produced by dissolving commercially available pentagalloylglucose into a suitable solvent.

Alternatively, the attractant for bone marrow stem cells containing pentagalloylglucose, for example, is produced by extraction of seeds of *oenothera tetraptera, paeonia lactiflora*, or the like.

The attractant for bone marrow stem cells may contain either cinnamtannin B1 or pentagalloylglucose, or may contain both cinnamtannin B1 and pentagalloylglucose.

Subsequently, an embodiment of a method for attracting bone marrow stem cells according to the present invention is described. In the method for attracting bone marrow stem cells of this embodiment, bone marrow stem cells are attracted by the aforementioned attractant for bone marrow stem cells.

Bone marrow stem cells are contained in bone marrow tissue, and can differentiate within the bone marrow tissue or migrate from the bone marrow tissue to another body tissue through the bloodstream.

Examples of the bone marrow stem cells include bone marrow mesenchymal stem cells capable of differentiating into mesodermal tissue cells such as chondrocytes, fat cells, and muscle cells, and hematopoietic stem cells capable of differentiating into blood cells such as erythrocytes and leukocytes.

Among these bone marrow stem cells, bone marrow mesenchymal stem cells can differentiate not only into mesodermal tissue cells, but also into ectodermal tissue cells such as nerves and endodermal tissue cells such as liver. As bone marrow stem cells to be attracted in the attraction method of the present invention, bone marrow mesenchymal stem cells are preferable because of the capability of differentiating into more various cells after the attraction.

In the method for attracting bone marrow stem cells, the bone marrow stem cells can be attracted by the attractant for bone marrow stem cells, for example, in vitro or in vivo.

Specifically, examples of the method for attracting bone marrow stem cells in vitro to be performed include a method, using a device provided with a membrane (film) having micropores passing therethrough in the thickness direction, with bone marrow stem cells being arranged on one side of the membrane and the attractant for bone marrow stem cells being arranged on the other side, for attracting the bone marrow stem cells toward the other side of the membrane over a specific time period.

Further, examples of the method for attracting bone marrow stem cells in vitro to be performed include a method, in which a part of disseminated bone marrow stem cells is scraped onto a slide glass, and a culture medium containing the attractant for bone marrow stem cells is applied to the scraped part, which is placed under culture conditions of bone marrow stem cells, thereby attracting the bone marrow stem cells to the scraped part.

The method for attracting bone marrow stem cells in vitro can be comparatively easily performed and thus may be implemented as a preliminary experiment, for example, in order to determine an optimal concentration of the attractant in the method for attracting bone marrow stem cells in vivo, which will be described below.

The degree of attraction of bone marrow stem cells in the aforementioned method for attracting bone marrow stem cells can be evaluated by staining the bone marrow stem cells and measuring the staining degree. Also, the attracted bone marrow stem cells can be evaluated by visual inspection.

On the other hand, examples of the method for attracting bone marrow stem cells in vivo to be performed include a method in which an aqueous gel containing the attractant for bone marrow stem cells is subcutaneously implanted into a normal mouse, followed by injection of mouse bone marrow stem cells into the vein of this mouse, and the mouse is bred for a specific time period, thereby attracting the bone marrow stem cells to the aqueous gel.

Further, examples of the method for attracting bone marrow stem cells in vivo to be performed include a method in which mouse bone marrow stem cells are transplanted into the bone marrow of a wound model mouse, and the attractant for bone marrow stem cells is applied to the wound site of the mouse, thereby attracting the bone marrow stem cells to the wound site.

The degree of attraction of bone marrow stem cells in the aforementioned method for attracting bone marrow stem cells can be evaluated by using mouse bone marrow stem cells expressing green fluorescent proteins (which hereinafter may be referred to also as GFP) as the bone marrow stem cells, and measuring the intensity of fluorescence in the attracted bone marrow stem cells.

Further, examples of the method for attracting bone marrow stem cells in vivo to be performed include a method in which a specific body tissue is treated to contain the attractant for bone marrow stem cells, thereby attracting bone marrow stem cells to the body tissue. More specifically, examples of the method for attracting bone marrow stem cells in vivo to be performed include a method in which skin epidermal tissue (such as stratum corneum) is allowed to contain the attractant for bone marrow stem cells, for example, by application, thereby attracting bone marrow mesenchymal stem cells present in the blood to the epidermal tissue.

Examples of the body tissue from which the bone marrow stem cells are attracted in the attraction method in vivo include various tissues such as muscle tissue, cartilage tissue, and liver tissue, other than epidermal tissue.

The method for attracting bone marrow stem cells in vivo is performed, for example, before the differentiation of bone marrow stem cells into various tissue cells, in order to accumulate bone marrow stem cells to the tissue.

The method for attracting bone marrow stem cells can be performed in vivo in humans, or in vivo in animals except humans. Preferably, the method for attracting bone marrow stem cells, for example, is performed for non-therapeutic use in vivo in humans for cosmetic purposes.

In the method for attracting bone marrow stem cells, an attractant in which cinnamtannin B1 or pentagalloylglucose is diluted to a suitable concentration can be used. The liquid to be used for dilution is not specifically limited. Examples thereof include water, normal saline, and a culture medium for bone marrow stem cells.

For example, the attractant for bone marrow stem cells containing cinnamtannin B1 is used at a cinnamtannin B1 concentration of, preferably, 1 to 100 μg/mL, more preferably, 10 to 40 μg/mL.

Further, the attractant for bone marrow stem cells containing pentagalloylglucose, for example, is used at a pentagalloylglucose concentration of, preferably, 0.01 to 1000 μg/mL, more preferably, 0.94 to 94 μg/mL.

The attractant for bone marrow stem cells and the method for attracting bone marrow stem cells according to this embodiment are as exemplified above. However, the present invention is not limited to the attractant for bone marrow stem cells and the method for attracting bone marrow stem cells exemplified above. Further, various embodiments that are generally employed for an attractant for bone marrow stem cells and a method for attracting bone marrow stem cells can be employed in the present invention, as long as the effects of the present invention are not impaired.

EXAMPLES

Next, the present invention is described further in detail by way of examples. However, the present invention is not limited to these examples.

Example 1

An attractant containing cinnamtannin B1 was produced by dissolving cinnamtannin B1 (Model No.: ALX-350-365-M005, manufactured by Enzo Life Sciences, Inc.) in a solvent (DMEM: Dulbecco's modified Eagle's medium) to give a concentration of 10 μg/mL.

Example 2

An attractant was produced in the same manner as in Example 1 except that the concentration of cinnamtannin B1 was 20 μg/mL.

Example 3

An attractant was produced in the same manner as in Example 1 except that the concentration of cinnamtannin B1 was 40 μg/mL.

Example 4

An attractant containing pentagalloylglucose was produced by dissolving pentagalloylglucose (Model No.: G7548, manufactured by Sigma-Aldrich Corporation) in a solvent (DMEM) to give a concentration of 94 ng/mL.

Example 5

An attractant was produced in the same manner as in Example 4 except that the concentration of pentagalloylglucose was 0.94 μg/mL.

Example 6

An attractant was produced in the same manner as in Example 4 except that the concentration of pentagalloylglucose was 9.4 μg/mL.

Example 7

An attractant was produced in the same manner as in Example 4 except that the concentration of pentagalloylglucose was 94 μg/mL.

The thus produced attractant for bone marrow stem cells of each example was used and evaluated by a cell attraction test in vitro. FIG. 1 schematically shows the process of the evaluation method. Hereinafter, the evaluation method is described in detail with reference to FIG. 1.

Cell Attraction Test In Vitro

The attractant for bone marrow stem cells of each example was prepared as a test sample. For comparison, a negative control sample and a positive control sample were prepared as well.

In the following description, FBS indicates bovine fetal serum. Further, P/S indicates 100 units of penicillin and 0.1 mg/mL of streptomycin. Further, the symbol (−) indicates no inclusion.

As a negative control sample, DMEM (Dulbecco's modified Eagle's medium) "FBS(−), P/S(−)" was prepared. That is, DMEM free from FBS and P/S was prepared.

Further, as a positive control sample, a DMEM solution with a 20 ng/mL PDGF-BB (platelet-derived growth factor PEPRO, manufactured by PeproTech, Inc.) concentration was prepared. That is, a solution in which PDGF-BB was diluted with DMEM to a concentration of 20 ng/mL was prepared.

On the other hand, mouse bone marrow mesenchymal stem cells (which hereinafter may be referred to also as mMSCs) were cultured to confluence and collected, and the stem cells were suspended in a liquid to $1 \times 10^7$ cells/ml. Thus, a cell suspension was prepared. As a liquid for the suspension of the cells, a 10 vol % FBS/DMEM "PIS(−)" was used. That is, a liquid free from P/S in which FBS was diluted with DMEM to a 10 vol % concentration was used as the liquid.

Next, a boyden chamber B (manufactured by Neuro Probe, Inc.) including a plurality of independent wells, each of which is partitioned into an upper well P and a lower well Q by a membrane M, as shown in FIG. 1(a), was prepared. Conditions were set so that one of the test samples, the negative control sample, and the positive control sample can be tested in the same boyden chamber B, and 28 μL of each sample was applied to the lower well of the chamber B. As the membrane M of the boyden chamber B, "Polycarbonate Membranes" (product name) (manufactured by Neuro Probe, Inc., with a pore size of 8 μm) were used.

Subsequently, 50 μL of each cell suspension was disseminated into the upper well P, and culture was performed under conditions of 37° C. and 5% $CO_2$ for 4 hours (see FIG. 1(b)).

After the 4-hour culture, mMSCs that have not migrated were stripped off using an attached filter wiper R, as shown in FIG. 1(c). Then, only the mMSCs that have migrated to below the membrane M were stained by Diff-Quik staining (using a kit manufactured by SYSMEX CORPORATION).

Further, the stained image was digitized and loaded into a computer, and the image was converted so that the color of the portion stained with blue was changed into white, thereby being binarized into black and white. Then, an average value of brightness within each well region was measured using a function of an image editing software (product name: Photoshop). The brightness of each test sample was compared to the brightness of the negative control sample and the positive control sample. Thus, the mMSC attraction activity of the attractant for bone marrow stem cells was evaluated.

Figure 2:
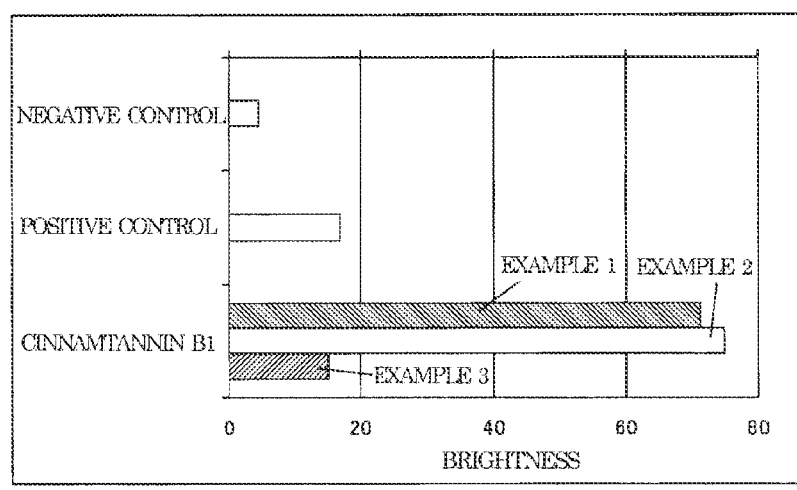
FIG. 2 is a chart showing the results of the cell attraction test in vitro.

FIG. 2 shows evaluation results of the attractants of Examples 1 to 3 as a graph of brightness. Further, FIG. 3 shows evaluation results of the attractants of Examples 4 to 7 in the same manner.

Figure 3:
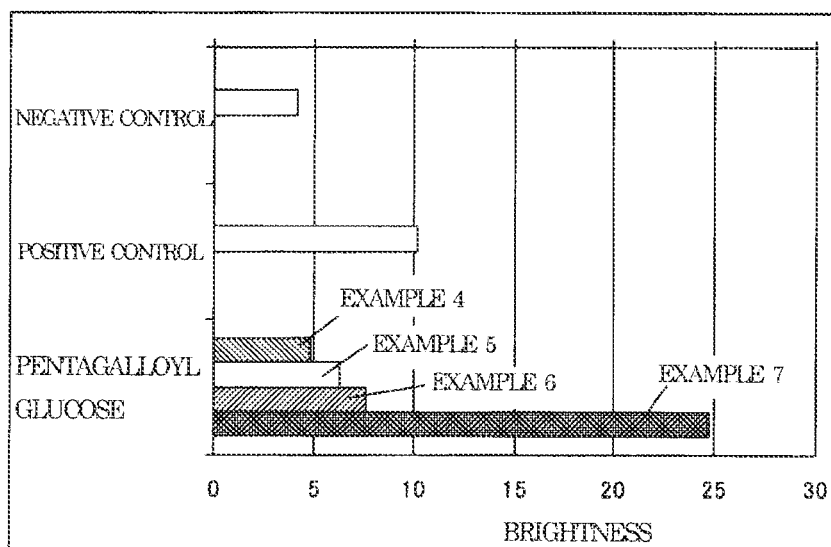
FIG. 3 is a chart showing the results of the cell attraction test in vitro.

As seen from FIG. 2 and FIG. 3, the attractants for bone marrow stem cells of Examples 1, 2, and 7 show particularly excellent performance to attract bone marrow stem cells.

Cell Attraction Test In Vivo of Mice

In order to evaluate the performance of the attractant for bone marrow stem cells to attract bone marrow stem cells in vivo of mice, living mice were subjected to experiments as follows. When a living mouse is wounded, bone marrow stem cells can accumulate around the wound portion through the bloodstream. Then, the bone marrow stem cells that have accumulated around the wound portion secrete cytokine, or the bone marrow stem cells that have accumulated around the wound portion differentiate into cells of the wound portion, thereby allowing the wound to be healed. Accordingly, it is expected that application of the attractant for bone marrow stem cells to the wound portion causes the bone marrow stem cells to be attracted to the wound portion, thereby accelerating the healing of the wound.

Method of Skin Regeneration Test (Wound Healing Test)

1. Experimental Material 1-a. Animals

Six genetically diabetic C57BLKs/J-dbm mice (BKS.Cg-+Leprdb/+Leprdb/Jcl*,db/db mice, female, 8 weeks old) were purchased from CLEA Japan, Inc. The mice were preliminarily bred for one week or more with ad libitum access to tap water and chow. Thereafter, the mice that are 9 weeks old were subjected to the test.

1-b. Wound Dressing

Polyurethane film dressing: 3M Tegaderm transparent dressing 1620 (product name), 6 cm×7 cm (manufactured by Sumitomo 3M Limited)

1-c. Elastic Bandage

Silkytex (product name) (manufactured by ALCARE Co., Ltd.)

1-d. Test Article

Basic fibroblast growth factor (bFGF) Trafermin (positive control): Fiblast Spray 250 (product name) (manufactured by KAKEN PHARMACEUTICAL CO., LTD.), with a concentration of 100 μg/mL Phosphate Buffer Normal Saline (PBS) (Negative Control)

Cinnamtannin B1 (120 μg/mL concentration, 40 μg/mL concentration) PBS solution

2. Method 2-a. Creation of Wound with Full-Thickness Skin Loss

All treatment for the mice was conducted under isoflurane inhalation anesthesia. Using an electric clipper and an electric shaver, the mice were sheared on the day before the wound creation.

The dorsal skin was cleaned with ethanol for disinfection, and a circular wound (with a diameter of 1.5 cm) with full-thickness skin loss was created at the back center, using surgical scissors.

2-b. Administration of Test Article

After the skin resection, 20 μL per site of bFGF (Trafermin), PBS, or cinnamtannin B1 was administered dropwise onto the wound surface. The administration was conducted in three mice per administration group.

After the administration, the wound surface was sealed with the aforementioned polyurethane film dressing, over which the aforementioned elastic bandage was applied. Replacement of the dressing and administration of the test article were performed three times per week, for four weeks. Thereafter, until about 60 days from the wound creation, replacement of the dressing was performed once a week. After an epithelium is formed, the dressing was not applied.

2-c. Observation

Wound Area Measurement

A picture of the back was captured three times per week, for four weeks, and the image was loaded into a PC. Thus, the wound area was measured using an image analysis software (product name: Image J). Thereafter, the wound area was measured once a week until about 60 days from the wound creation.

Figure 4:
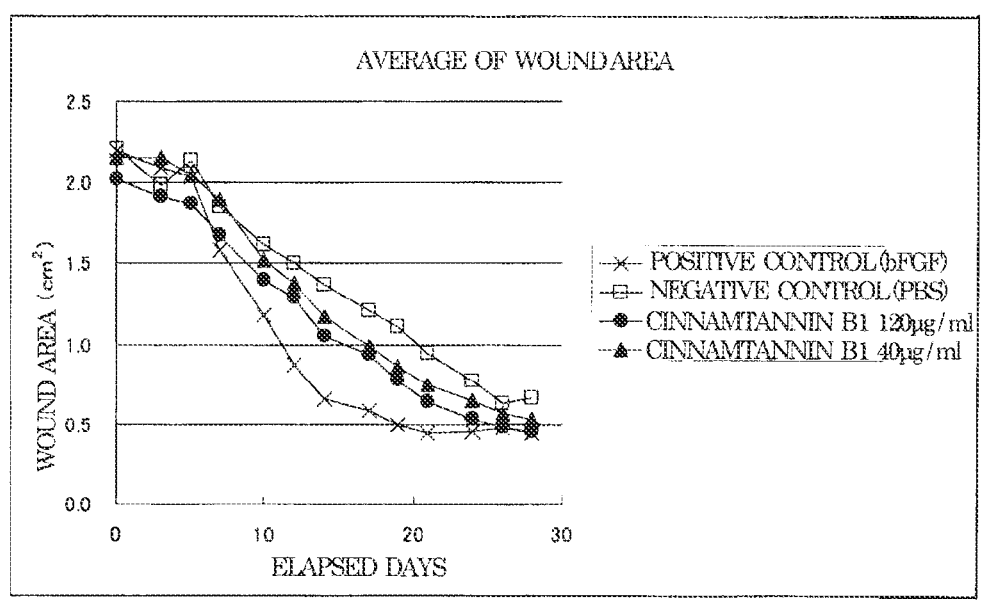
FIG. 4 is a graph showing the results of the cell attraction test in living mice.

FIG. 4 shows the results of the aforementioned wound area measurement in vivo of mice.

As seen from FIG. 4, it is inferred that bone marrow stem cells were attracted to the wound portion by the attractant containing cinnamtannin B1 for bone marrow stem cells, as a result of which the healing of the wound was accelerated.

As described above, the attractant for bone marrow stem cells and the method for attracting bone marrow stem cells of the present invention have advantageous effects of having excellent performance to attract bone marrow stem cells.

INDUSTRIAL APPLICABILITY

The attractant for bone marrow stem cells and the method for attracting bone marrow stem cells of the present invention, for example, are used for attracting bone marrow stem cells generated in bone marrow to a specific body tissue before the differentiation of bone marrow stem cells in the specific body tissue. That is, the attractant for bone marrow stem cells and the method for attracting bone marrow stem cells of the present invention is suitably used for attracting bone marrow stem cells circulating in the body through the bloodstream to a specific body tissue and accumulating them therein, for example, by treating the specific body tissue to contain the attractant.

REFERENCE SIGNS LIST

B: Boyden Chamber
P: Upper Well
Q: Lower Well
M: Membrane
R: Filter Wiper

The invention claimed is:

1. A method of treating a skin wound, comprising attracting bone marrow stem cells by application of a bone marrow stem cell attractant comprising cinnamtannin B1 to a wound site of a skin epidermal tissue of a mammal.

2. The method of claim 1, wherein the bone marrow stem cell attractant further comprises at least one of one or more polyhydric alcohols and a preservative.

3. The method of claim 1, wherein the method accelerates healing of the wound.

4. The method of claim 1, wherein the skin is human skin.

5. The method of claim 1, comprising attracting bone marrow stem cells present in the blood.

* * * * *